(12) United States Patent
Bates et al.

(10) Patent No.: US 9,408,681 B2
(45) Date of Patent: Aug. 9, 2016

(54) TOOTHBRUSH USAGE MONITORING

(75) Inventors: Susan Bates, Wirral (GB); Vasile Cosmin Lazar, Grenoble (FR); Derek Guy Savill, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 698 days.

(21) Appl. No.: 13/820,551

(22) PCT Filed: Aug. 5, 2011

(86) PCT No.: PCT/EP2011/063514
§ 371 (c)(1),
(2), (4) Date: Mar. 4, 2013

(87) PCT Pub. No.: WO2012/034786
PCT Pub. Date: Mar. 22, 2012

(65) Prior Publication Data
US 2013/0166220 A1 Jun. 27, 2013

(30) Foreign Application Priority Data
Sep. 15, 2010 (EP) ..................................... 10176763

(51) Int. Cl.
*A61C 19/04* (2006.01)
*A46B 15/00* (2006.01)
*A61C 17/22* (2006.01)

(52) U.S. Cl.
CPC .............. *A61C 19/04* (2013.01); *A46B 15/0002* (2013.01); *A46B 15/0006* (2013.01); *A61C 17/221* (2013.01)

(58) Field of Classification Search
CPC ............... A46B 15/00; A46B 15/0002; A46B 15/0006; A46B 15/0008; A46B 15/0038; A46B 15/004; A46B 9/04; A61C 17/221
See application file for complete search history.

(56) References Cited

U.S. PATENT DOCUMENTS

| 6,536,068 B1 | 3/2003 | Yang et al. |
| 2002/0183959 A1 | 12/2002 | Savill et al. |

(Continued)

FOREIGN PATENT DOCUMENTS

| CN | 201032913 | 3/2008 |
| DE | 102005014095 | 10/2006 |

OTHER PUBLICATIONS

Claessen et al., Designing Interventions to Improve Tooth Brushing, 2008, International Dental Journal, vol. 58, No. 5, pp. 307-320.*

(Continued)

*Primary Examiner* — Toan Le
(74) *Attorney, Agent, or Firm* — Greenberg Traurig, LLP

(57) ABSTRACT

The invention provides a system suitable for monitoring the usage of a toothbrush, the system comprising: (a) a toothbrush; (b) a sound sensor which is located in or on the toothbrush; (c) a programmable data logger which is located in or on the toothbrush, the data logger incorporating a motion sensor and a data store for the logging of data; (d) switching means for triggering the operation of the sound sensor in response to initial signals of toothbrush motion generated by the motion sensor, and (e) a data analysis device which is adapted to analyze data transmitted or acquired from the system to provide information about tooth brushing behavior; in which the duration of data logging is controllable in response to the combined signals received from the sound sensor and the motion sensor respectively.

10 Claims, 2 Drawing Sheets

(56) References Cited

U.S. PATENT DOCUMENTS

| | | |
|---|---|---|
| 2004/0000017 A1 | 1/2004 | Kumagai |
| 2007/0190509 A1 | 8/2007 | Kim |
| 2008/0102953 A1 | 5/2008 | Schultz |
| 2008/0141476 A1 | 6/2008 | Gatzemeyer et al. |
| 2009/0092955 A1 | 4/2009 | Hwang |
| 2009/0241278 A1 | 10/2009 | Lemchen |
| 2009/0291422 A1* | 11/2009 | Puurunen .......... A46B 15/0006 434/263 |
| 2009/0307859 A1 | 12/2009 | Mottram et al. |
| 2009/0320227 A1 | 12/2009 | Cohen et al. |

OTHER PUBLICATIONS

Claessen, et al, Designing interventions to improve tooth brushing, Intl Dental Journal, Jan. 1, 2008, 307-320, 58, No. 5, GB.

International Search Report, PCT/EP2011/063514, mailed Jan. 24, 2012, 3 pp.

European Search Report, EP 10 17 6763, dated Mar. 21, 2011, 2 pp.

* cited by examiner

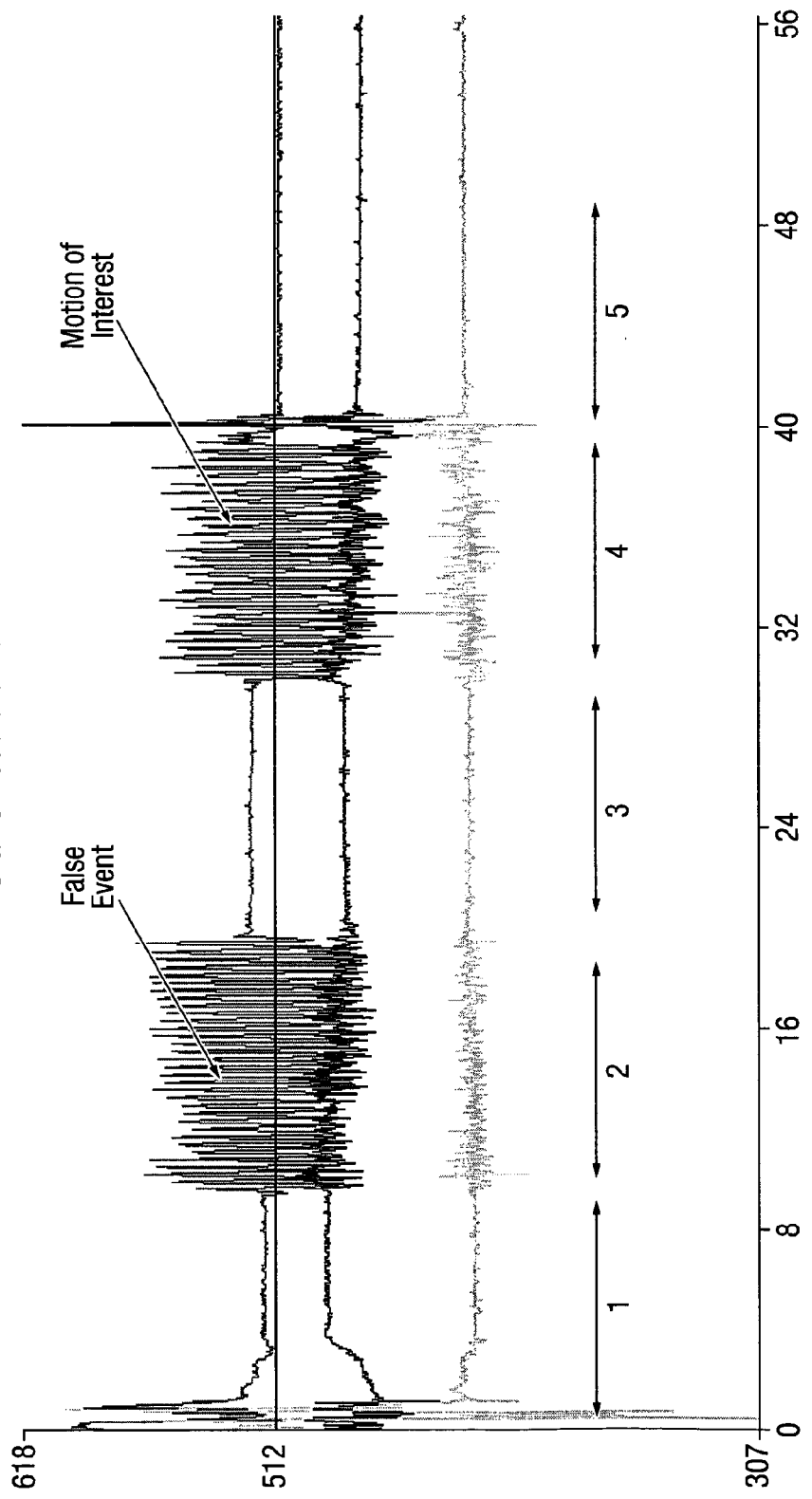

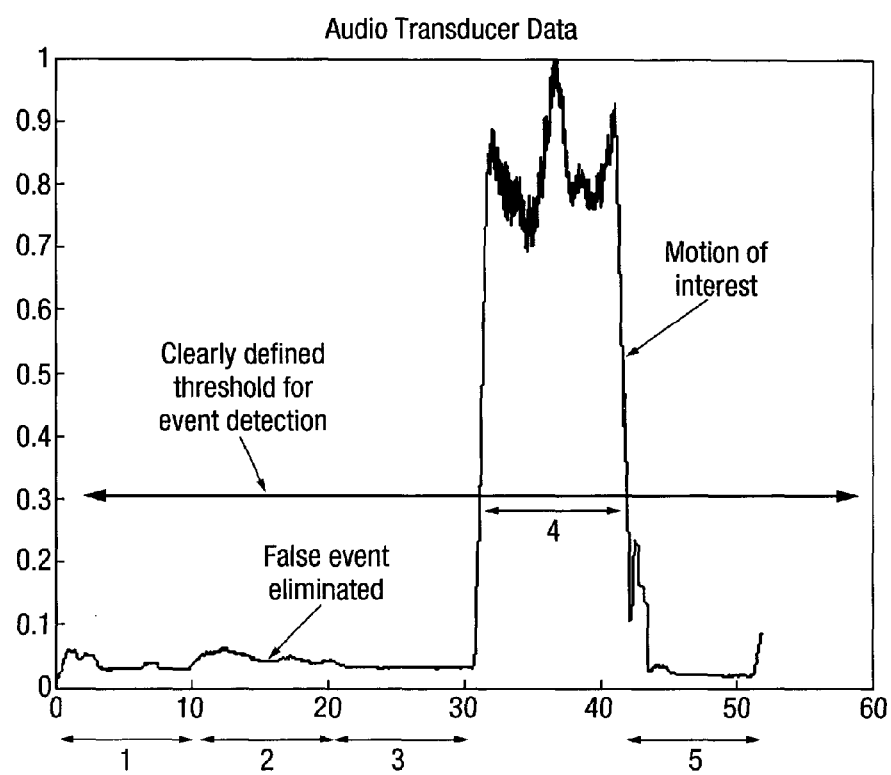

TOOTHBRUSH USAGE MONITORING

FIELD OF THE INVENTION

The present invention relates to toothbrush usage monitoring.

BACKGROUND OF THE INVENTION AND PRIOR ART

There is little doubt about how people can contribute to good oral health and hygiene through their own behaviour. In essence this concerns brushing teeth twice a day for at least two minutes with a fluoride containing toothpaste. Still this elementary behaviour is not as widely and fully practised as dentists and health organisations would like it to be. Behaviour change and interventions to evoke change are essential to achieve this.

The ability to monitor various aspects of consumers' existing tooth brushing behaviour is key to developing effective intervention strategies and evoking behaviour change.

Self-report and observation have been widely used in medical, psychological and market research to understand behaviour. Both methods have disadvantages. For example, people are very often unable to report key aspects of their behaviour, or may be influenced by what they think the researcher would like to hear. When an individual is being observed, the presence of an observer is likely to affect the very behaviour they are there to observe.

In order to capture tooth brushing behaviour of individuals without having to revert to self-report or observation, a toothbrush has been developed with a compartment in the handle which contains a small programmable data logger based on a 3-axial accelerometer, including memory and battery (*International Dental Journal* (2008); 58: 307-320). Because it is hidden within the toothbrush, people quickly forget that it is there and therefore revert to naturalistic behaviour. While in the toothbrush the logger will check the acceleration on each of the x, y and z axes, and will initiate recording when it detects acceleration above a pre-set threshold. It will then record acceleration data in three axes at a pre-specified frequency creating a record of pre-determined length. At the end of the record the logger will stop recording unless it is still experiencing above threshold acceleration, in which case, it will create another record. For each record the logger will store the data for subsequent downloading and analysis.

Analysis of the stored data is often a complex procedure, because any motion with sufficient acceleration to trigger the logger will trigger data capture. This may or may not be the motion of interest, and with each false event captured, device power and memory capacity are reduced. Also, a further data analysis step is required to filter the desired events and remove any false events.

The present inventors have found that this problem can be solved by using a sound sensor in combination with a motion sensor such as the accelerometer based logger described above. Combining information from the sound sensor enables reduced recording of false events, leading to reduced energy consumption, lower power and memory requirements, greater device efficiency and greater ease of data analysis. This is especially advantageous in consumer behaviour analysis settings, where data capture may be required over prolonged periods of time. Also, small low power devices are less likely to interfere with normal consumer activity, so the data collected is more representative of real behaviour.

US2008/0102953 describes a toothbrush for encouraging children to brush on a regular basis, which may include a motion sensor and may also include an audio processor communicatively linked to an input audio transducer (e.g. microphone). The sensor data is processed to generate gaming signals that are communicated to a gaming device as gaming inputs. There is no description of any functional interaction between the sound and motion sensors in this device, nor any suggestion of reduced recording of false events or reduced energy consumption.

SUMMARY OF THE INVENTION

The invention also provides a system suitable for monitoring the usage of a toothbrush, the system comprising:
(a) a toothbrush;
(b) a sound sensor which is located in or on the toothbrush;
(c) a programmable data logger which is located in or on the toothbrush, the data logger incorporating a motion sensor and a data store for the logging of data;
(d) switching means for triggering the operation of the sound sensor in response to initial signals of toothbrush motion generated by the motion sensor, and
(e) a data analysis device which is adapted to analyse data transmitted or acquired from the system to provide information about tooth brushing behaviour;
in which the duration of data logging is controllable in response to the combined signals received from the sound sensor and the motion sensor respectively.

The invention also provides a method for monitoring the usage of a toothbrush, including the steps of:
(a) acquiring data from a sound sensor which is located in or on the toothbrush;
(b) acquiring data from a programmable data logger which is located in or on the toothbrush, the data logger incorporating a motion sensor and a data store for the logging of data,
(c) analysing the data so acquired to provide information about tooth brushing behaviour;
characterised in that the operation of the sound sensor is triggered in response to initial signals of toothbrush motion generated by the motion sensor, and in that the duration of data logging is controllable in response to the combined signals received from the sound sensor and the motion sensor respectively.

DETAILED DESCRIPTION OF THE INVENTION

Typically the toothbrush will include a handle, a neck and a brush region extending from the neck, the brush region including brushing elements such as bristles, extending from a base.

A sound sensor is located in or on the toothbrush.

The sound sensor is adapted to detect sounds associated with the use of the toothbrush and to generate signals corresponding to the detected sounds. Typically, the sound sensor is an audio transducer, such as a microphone. Suitable microphones include contact microphones, otherwise known as pickup or piezo (piezo-electric) microphones, which are designed to transmit audio vibrations through solid objects.

The sound sensor may be located anywhere in or on the toothbrush. In a preferred construction, the toothbrush is provided with a cavity, such as a hollow handle, for accommodating the sound sensor. The sound sensor could also be incorporated within the programmable data logger.

A programmable data logger is located in or on the toothbrush. In a preferred construction, the toothbrush is provided with an outer casing, onto which the programmable data logger may be firmly attached.

The programmable data logger generally incorporates a power source, which is typically a DC power source such as a small (e.g. 3V) battery. To prolong battery life, a capacitor may be included. Alternatively the programmable data logger may be at least in part solar powered.

The motion sensor incorporated in the programmable data logger is adapted to detect motion of the toothbrush and to generate signals corresponding to the detected motion. Typically, the motion sensor is an accelerometer capable of sensing accelerations along one or more axes. The accelerometer may be capable of sensing accelerations along three orthogonal axes. Any suitable tri-axial accelerometer could be used or alternatively, two 2-axis ones mounted at right angles capable of sensing 3-dimensional acceleration data. Alternatively any other suitable motion sensor may be used. The motion sensor may be analogue or digital.

The data store incorporated in the programmable data logger preferably incorporates erasable non-volatile memory. Erasable (rewritable) memory allows re-use of the data logger. Non-volatile memory is preferable because this means the memory is protected in case of a loss of power (e.g. in the case of battery powered devices, when the battery loses power).

The data logger is programmable, and typically contains a programmable computing device, such as a microprocessor (e.g. a microcontroller) which is capable of reading and executing program instructions to control the various components within the toothbrush usage monitoring system of the invention.

In a typical toothbrush usage monitoring method using the system of the invention, the programmable data logger is first connected to a computer (typically a PC or similar). Programming will provide key operational parameters such as the activation and the duration of the data logging process.

The programmed data logger is then installed, either in or on the toothbrush. Preferably it is firmly attached to an outer casing of the toothbrush.

When initial signals corresponding to toothbrush motion are detected, switching means trigger the operation of the sound sensor. A preferred switching means is a tilt switch, since this is small, low power and can detect motion or orientation simply.

The data logger checks for motion of the toothbrush, indicated by signals generated by the motion sensor (typically an accelerometer or similar). Data is also acquired from the sound sensor, activated by the initial detection of toothbrush motion as described above.

The duration of data logging is controllable in response to the combined signals received from the sound sensor and the motion sensor respectively.

The inventors have found that the data acquired from the sound sensor provides a surprisingly reliable means of indicating whether actual tooth brushing is taking place, as opposed to merely shaking or moving the toothbrush without contacting the teeth (a false event).

Accordingly, in the system of the invention the data logger will typically be programmed so that data logging only takes place when the signals received from the sound sensor and the signals received from the motion sensor are each registered above pre-defined thresholds of duration or intensity.

In this way, the system is able to operate in an "active data capture" mode for capturing the activity of interest, but is also able to revert to a "low power mode" at other times. This enables reduced recording of false events, leading to reduced energy consumption, lower power and memory requirements, greater device efficiency and greater ease of data analysis.

The data acquired by the system of the invention is analysed by a data analysis device to provide information about tooth brushing behaviour.

Typically, the data acquired by the system of the invention is downloaded to a remote data analysis device such as a computing device (e.g. a PC). Alternatively the data may be transmitted to the data analysis device by cellular telephony or wireless LAN technology, preferably "Wi-Fi" (wireless fidelity) enabling easy, fast communication via internet.

The analysis can provide information about various aspects of tooth brushing behaviour, such as the force or pressure applied during the tooth brushing process, the speed of the tooth brushing action, the directionality of the tooth brushing action, the duration of individual tooth brushing events, the frequency of individual tooth brushing events per day or a combination of any of the above.

Advantageously such data analysis can take place conveniently e.g. in a laboratory many miles away with minimal interference in the toothbrush users' life.

EXAMPLE

Data was simultaneously recorded from an audio transducer device placed inside the cavity of a toothbrush, and an 3-axis accelerometer based logging device firmly attached to the outer casing of the toothbrush.

A brushing sequence was manually performed as given in the table below:

| Sequence | Event | Duration |
| --- | --- | --- |
| 1. Pick up and hold | Toothbrush picked up and held stationary | 10 seconds |
| 2. Shake | Toothbrush shaken to simulate tooth brushing (horizontal scrubbing) but with no contact with the teeth | 10 seconds |
| 3. Hold | Toothbrush held stationary | 10 seconds |
| 4. Brushing | Tooth brushing (horizontal scrubbing) - brush filaments in contact with model dentition | 10 seconds |
| 5. Put down - at rest | Brush put down onto a hard surface and left at rest | 10 seconds |

The appended FIG. 1 illustrates the 3-axis accelerometer data acquired from performance of the above sequence.

The appended FIG. 2 illustrates the corresponding audio transducer data acquired simultaneously from the performance of the above sequence.

The 10-second events "1" to "5" as described in the table are indicated on the horizontal axis of each graph.

The data clearly shows the ability of the audio transducer to eliminate false events. In the case of the 3-axis accelerometer data, the false event "2" has the same acceleration and frequency as the event of interest "4", as shown in FIG. 1. However the audio transducer can discriminate between "2" and "4", as shown in FIG. 2.

The invention claimed is:

1. A system suitable for logging data relating to usage of a toothbrush, the system comprising:
   (a) a toothbrush;
   (b) a sound sensor which is located in or on the toothbrush which is configured to detect sounds associated with the use of the toothbrush and to generate signals corresponding to the detected sounds;
   (c) a programmable data logger which is located in or on the toothbrush, the data logger incorporating a motion sensor and a data store for the logging of data for analysis to provide information about tooth brushing behaviour;

(d) switching means configured to trigger operation of the sound sensor to detect sounds in response to initial signals of toothbrush motion generated by the motion sensor, and wherein a duration of data logging is configured to be controlled in response to a combination of the signals received from the sound sensor and the signals received from the motion sensor.

2. The system according to claim 1, wherein the toothbrush includes a handle, a neck and a brush region extending from the neck, the brush region including brushing elements such as bristles, extending from a base.

3. The system according to claim 1, wherein the sound sensor is an audio transducer.

4. The system according to claim 3, wherein the sound sensor is a microphone.

5. The system according to claim 1, wherein the motion sensor is an accelerometer capable of sensing accelerations along one or more axes.

6. The system according to claim 1, wherein the data store incorporates erasable non-volatile memory.

7. The system according to claim 1, wherein the programmable data logger is programmed so that data logging only takes place when the signals received from the sound sensor and the signals received from the motion sensor are each registered above pre-defined thresholds of duration or intensity.

8. The system according to claim 1, wherein the switching means is a tilt switch.

9. The system according to claim 1, wherein the sound sensor is incorporated within the programmable data logger.

10. A method for logging data relating to usage of a toothbrush, including the steps of:

(a) acquiring data from a sound sensor configured to detect sounds associated with the use of the toothbrush and to generate signals corresponding to the detected sounds, wherein the sound sensor is located in or on the toothbrush;

(b) logging data by a programmable data logger which is located in or on the toothbrush, the data logger incorporating a motion sensor and a data store for the logging of data for analysis to provide information about tooth brushing behaviour;

the wherein operation of the sound sensor to detect sounds is triggered in response to initial signals of toothbrush motion generated by the motion sensor, and wherein a duration of data logging is controlled in response to a combination of the signals received from the sound sensor and signals received from the motion sensor.

* * * * *